US00PP09852P

United States Patent [19]

Bost

[11] Patent Number: Plant 9,852

[45] Date of Patent: Apr. 8, 1997

[54] HIBISCUS PLANT NAMED 'BOST HYBRID NO. 2'

[76] Inventor: Georgia A. Bost, 1209 Pine Chase, Houston, Tex. 77055

[21] Appl. No.: 539,026

[22] Filed: Jun. 16, 1995

[51] Int. Cl.[6] ..... A01H 5/00

[52] U.S. Cl. ..... Plt./67.8

[58] Field of Search ..... Plt./67.8

[56] References Cited

U.S. PATENT DOCUMENTS

P.P. 9,555 5/1996 Morrison ..... Plt./67.8

*Primary Examiner*—James R. Feyrer

*Attorney, Agent, or Firm*—Martin L. McGregor

[57] ABSTRACT

An herbaceous perennial Hibiscus plant having numerous large polypetalous flowers with blushing white petals, overlapping petal arrangement, a dark red eye, essentially white buds, and medium-sized well-branched, upright plants with one or three-lobed leaves of light to medium green color.

2 Drawing Sheets

HISTORICAL NOTE

As of August 1996, there are a total of 20 plant patents granted for the species Hibiscus in the United States of America. The earliest patented hibiscus plant (U.S. Plant Pat. No. 835), identified in the records simply as 'Mallow', was selected from a population having within its genetic background *Hibiscus laevis* (formerly *militaris*), *H. coccineus*, and *H. moscheutos*. This early improved plant was characterized by having smooth, deeply cut leaves, as attaining shrub height of medium size, of having medium sized (6–8 inch) flowers with deep red, imbricated flower petals and by being adapted for culture in the temperate zone.

Within the remainder of the existing patents, 10 are *H. "rosa-sinensis"* types developed by Frank Moser; three more are also *H. rosa-sinensis* varieties, developed by Roberta Ludick; and one is a variegated sport of *H. paeoniflorus*, selected by Harold Hillis. All plants in this group of patents are developed from tropical, mostly pan-Pacific species that do not survive unprotected north of USDA Zone 10.

The novel plant invention described herein is developed from the suite of perennial hibiscus species belonging to Hibiscus Section meunchhusia (O.J. Blanchard, 1976; P.A. Fryxell, 1988) that are native to the continental United States. There are four recognized species in this Section (*H. coccineus, H. dasycalyx, H. laevix*, and *H. moscheutos*) one of which has several recognized subspecies: *H. moscheutos moscheutos, H. m. palustris*, and *H. m. grandiflorus*. The other species of hibiscus native to the conterminous U.S. and Hawaii are not genetically compatible with these four species.

All species of hibiscus in Section Meunchhusia are wetland plants and, although tolerant of even severe drought (via semi-dormancy), perform best under adequate moisture conditions. They tolerate—rather than require—saturated soil and/or standing water conditions and compete best *in the wild* on the borders of water bodies where periodic fires reduce compeition from woody species. Consquently, they make excellent low-maintenance border plantings around water features and grow well in all climates where adequate rainfall and/or irrigation is available. As a general rule, the farther north the planting, the less water is required and the shorter the plant will be at maturity.

There are currently only six patented varieties of this type of hibiscus: 'mallow' (Hemmings, U.S. Plant Pat. No. 835), 'Lady Baltimore' (Darby, U.S. Plant Pat. No. 4,271), 'Anne Arundel' (Darby, U.S. Plant Pat. No. 5,209), 'Sweet Caroline' (Winters, U.S. Plant Pat. No. 7,608), 'Quatro Rojo' (Bost Hybrid No. 1, U.S. Plant Pat. No. 9,311), and 'Pink Wonder' (Morrison, U.S. Plant Pat. No. 9,555). The first four of these plants were developed from East Coast USA populations of Hibiscus species (or subspecies) *H. moscheutos, H. moscheutos* ssp. *palustris*, and/or *H. laevis*, in various combinations with the Florida species, *H. coccineus*. The sixth was developed from *H. moscheutos, H. m. palustris* and *H. laevis*. 'Quatro Rojo' was developed from progeny of crosses made with a population of *H. laevis* native to Texas, in various combinations with *H. coccineus* and *H. moscheutos*×'Southern Belle'; the latter was developed from U.S. native hibiscus by Japanese breeders many years ago and marketed in the USA, originally through seed catalogs. 'Southern Belle' is dominated by *H. moscheutos* characteristics.

The general growth habit of Section Meunchhusia hibisci is characterized by long, straight, light-weight canes which arise annually from a perennial crown. Once established, crowns generally bud two to three—more rarely, four—new shoots from the base of each of the preceeding season's canes. Side branching occurs in the upper half to one-third of the cane (depending on species dominance), given sufficient length of growing season, but generally is not initiated until first bud set has occurred. Forking of canes occurs only if the green cane is cut or broken off.

Crowns frequently go through cycles of cane production that are a function of the age of the crown and the amount of crowding in the center of the crown. Typically, new canes are more abundant on the outside of the crown, until enough space has developed in the center to once again allow central cane growth. Plants can be propagated effectively either from crown division or from cuttings; for either method, rooting hormone is optional.

Cane production is typically much more vigorous (in both size and number) in hybrids than in the native specimens, all other factors being equal. In general, a new seedling will produce only one cane, due to the time it takes for the plant to mature enough to begin flower budding. Second year crowns generally break dormancy with 2–3 canes, but may produce more given a sufficiently long growing season.

Third year crowns typically produce 6–9 canes, and so on. Number and vigor of canes is also dependent on spacing of the individual specimens and the size of the container in which it is grown, as well as length of growing season where grown, and the genetic background of the parental stock from which the cultivar was developed. Plants become severly stunted when container size is too small for the crown size. A well developed crown will frequently outweigh its canes.

Spacing of leaves, internodal length and leave shape are a function of species genome, as is bloom onset and distribution, abscission point, and presence or absence of foliage on bloom pedicels. however, these characters *in hybrids* show a wide range of intermediate characters and may or may not be distictive for a given hybrid type.

Overall plant presentation ranges from *H. moscheutos* on one extreme, with an essentially spherical presentation (consisting of relatively short canes and widely-spaced but large, cordate leaves), to *H. coccineous* on the other extreme, with an essentially vase-shaped or V-shaped presentation of 5-lobed, highly-dissected, cannabis-like leaves. *H. laevis* and *H. dasycalyx* have the shortest internode size with leaves that are predominantly 3-lobed and hastate, with an essentially vase-shaped habit. *H. moscheutos* flower buds tend to produce a panicle-like effect due to the extreme fore-shortening of flowering internodes and the relatively short period of flowering for this species (1–2 months, even in Zone 9). The other three species have well-spaced flowers that follow the same rotation as the leave nodes and bloom for 2–7 months, depending on soil temperatures and frost dates for the region in which they are grown, and genetic dormancy for the region of origin.

On the average, a given flower for any of these genomes will last only one day; however, cool nights followed by cool mild day(s) commonly delay flower drop for an additional day or two, especially if fertilization has not occurred. The farther north the plants are grown, the more likely the flowers are to last more than one day. Thus, the ability of a given flower to last more than one day is not a particularly destinctive character within this group. Similarly, the more northern USDA Zones will have shorter and more concise bloom periods and may frequently experience frost before "natural" dormancy begins. The regional affect on the genetic component of dormancy appears to apply primarily to the breaking of dormancy in Spring, not to winter onset.

In Zone 9, dormancy almost always occurs before frost, although some plants have still been observed to bloom as late as the end of January, during especially mild winters. Dormancy appears to be triggered by soil temperature, but also shows a strong genetic component related to the climatic region of the source genome. Dormancy or semi-dormancy can also be triggered by severe drought. A normal winter-triggred dormant period seems to be beneficial for this group of hibiscus, as specimens grown in tropical climates or in heated greenhouses year-round loose vigor, are less resistant to disease and pests, and eventually die prematurely (five years or less).

The average life span of the perennial crowns of these species and their hybrids has not, to our knowledge, been documented. Anecdotal evidence suggests crown life-spans of more than 25 years and, barring catastrophic events or disease, could be more than 100 years.

BACKGROUND OF THE NEW PLANT

The breeding program which produced the novel plant invention described herein and named 'Bost Hybrid No.2' extended over a period of some 9 years. 'Bost Hybrid No.2' originated as a seedling selected from progeny of cross pollination between (1) a breeding line derived from crossing the commercially available *H. moscheutos* var. 'Southern Belle' and *H. laevis* BOST×® selection 'Houston-White'; (2) a breeding line derived from crossing *H. laevis* BOST ×® selection 'Houston-White' and *H. coccineus;* and, (3) a breeding line derived from crossing *H. coccineus* and *H. moscheutos* var. 'Southern Belle'.

Unfortunately, the original tag documenting the pod and pollen parents of the seedling was unreadable a the time the plant was evaluated and selected. 'Bost Hybrid No.2' clearly shows characteristics of at least two of the three original parent (P1) genomes used to establish this breeding program.

The objective of the breeding program which produced the novel plant of this invention was primarily to develop a plant that was suitable for inclusion in a horticultural group to be marketed as a series of BOST×® horticultural hybrids commemorating the first ladies of United States presidents and having the following characteristics:

(a) a medium size plant suitable for cultivation, with good form and reliably upright havit, and abundant flowers.
(b) Decorative foliage of a pleasing shade of green and productive, well-placed flowers and pods suitable for both horticultural and agricultural applications;
(c) Attractive, well-formed, medium-sized white flowers that are distinctively blushed with pink, that are well-posed on the plant, and that remain open for most of the day (two days in cooler weather).

SUMMARY OF THE INVENTION

The present invention comprises a new and distinct cultivar of herbaceous perennial Hibiscus hybrid hereinafter referred to by the cultivar name 'Bost Hybrid No. 2'. It was a seedling selected by Georgia A. Bost in July 1992 from a seedling population grown at her nursery, The Village Botanica, Inc., at 7500 Westview Drive, Houston, Tex. She is the owner of the mother plant and clones and controls all propagations of it. The new plant produced its first flower in the summer of 1992 and, because of the size and shape of the plant and the subtile coloring of the flower, its attractive foliage and controlled habit, it was selected for reproduction and testing. Asexual propagation of this new plant by cuttings was carried on at The Village Botanica, 7500 Westview Drive, Houston, Tex and at JJL Greenhouses, Inc., 1449 Brittmoore, Houston, Tex in 1994 under exclusive contract to The Village Botanica, Inc. Observation of the asexual progeny of the original plant has demonstrated that this new and distinct variety has fulfilled the objectives and that its distinctive characteristics are firmly fixed and hold true from generation to generation vegetatively propagated from the original clone.

The new and distinct cultivar is of value for its floral display, produced from late May until late November (or frost), depending upon USDA zone in which it is cultured, environmental conditions and culture methods; and for the landscape value of the entire plant; and as a source of plant materials for commercial and agricultural products.

BRIEF DESCRIPTION OF THE DRAWINGS

This new cultivar of perennial Hibiscus is illustrated by the accompanying full color photographic drawing which shows.

DETAILED DESCRIPTION OF THE NEW PLANT

Figure 1:
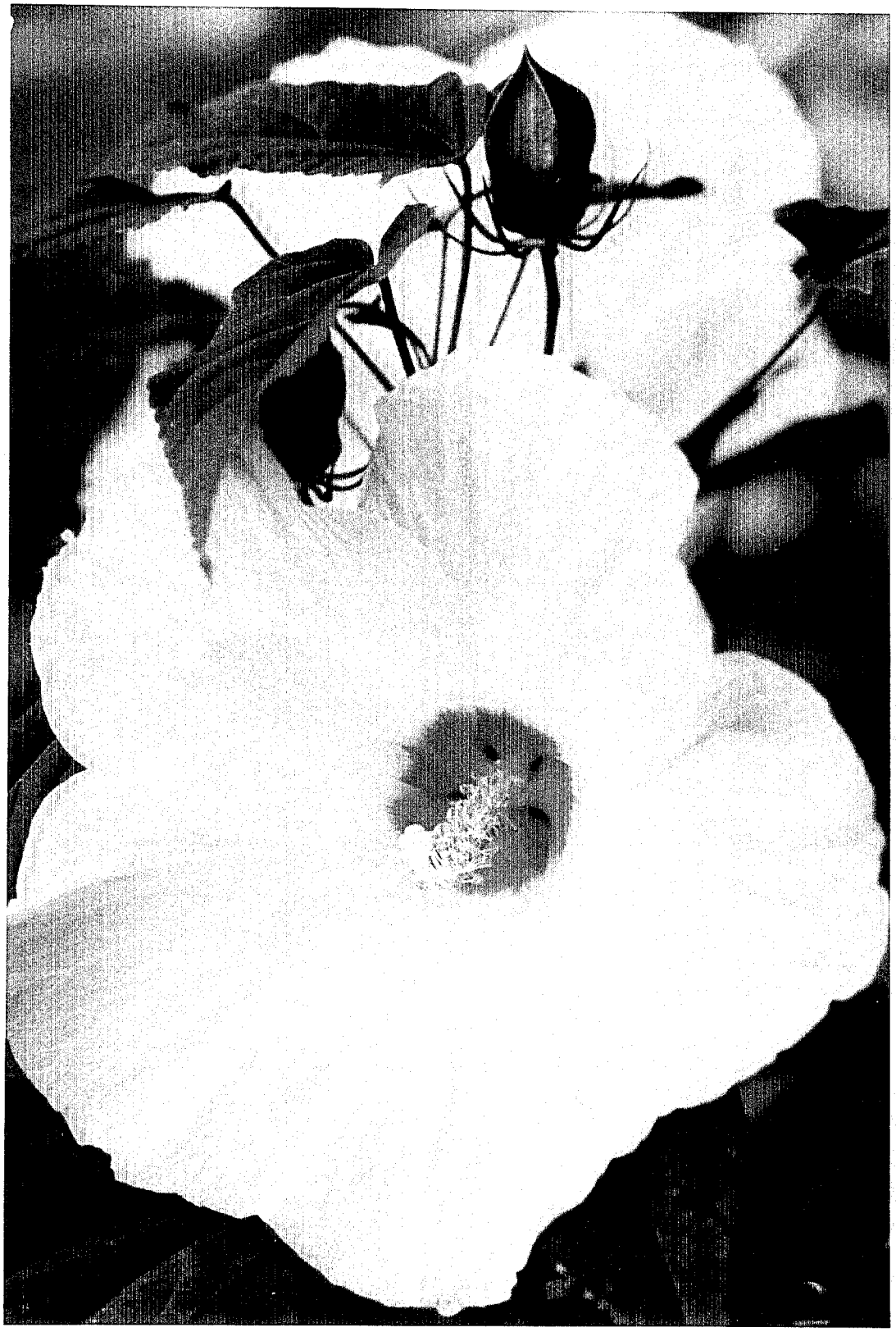
FIG. 1—a fully opened flower and some typical leaves and buds, the colors being as true as can reasonably be done by conventional photographic procedures. The drawing depicts the blossom in mid-afternoon, when the flower is more deeply blushed.
Figure 2:
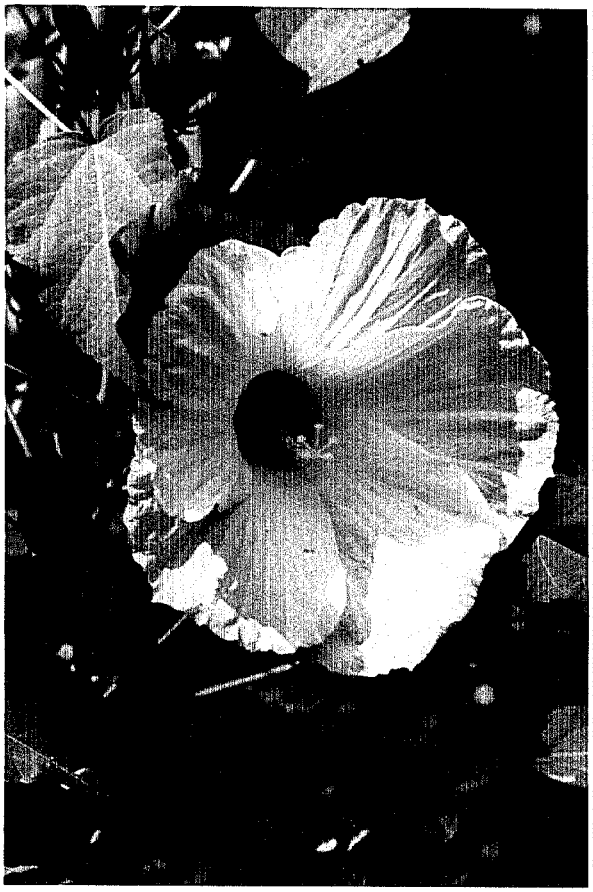
FIG. 2 shows the same plant and flower under different lighting conditions and earlier in the day.

The following is a detailed description of the new variety, color terminology being in accordance with The Royal Horticultural Society Colour Chart (indicated by initials R.H.S.-number) for the closest match or with ordinary dictionary significance.

THE PLANT

Type: Root-hardy, herbaceous perennial.

Classification: Hybrid variety of Hibiscus, Section Meunchhusia (Fryxell, 1988).

Origin: Seedling.

Parentage: Is known to be a selection from BOST×® breeding population from cross pollination between (1) a breeding line derived from crossing the commercially available *H. moscheutos* var. 'Southern Belle' with *H. laevis* BOST×® selection 'Houston-White'; (2) a breeding line derived from crossing *H. laevis* selection 'Houston-White' with; and (3) a breeding line derived from crossing *H. coccineus* with *H. moscheutos* var. 'Southern Belle'.

Propagation: Holds its distinguishing characteristics through succeeding propagations by cuttings and divisions.

Form: Bushy annual growth from perennial root and root crowns,

Mature habit: Upright and much branched.

Growth: Vigorous.

*Foliage.*—Arrangement — Alternate. In general, not distinctive and fairly typical within the genera used to derive the plant. Colors are closest to the R.H.S. codes listed below for the respective tissues.

*Form.*—1 and/or 3-lobed, hastate, palmately veined.

*Size.*—average is 3–9 inches along primary vein, approx. 5 inches wide across lateral veins. Central lobe always larger than any laterals. Laterals, when present, always with two primary veins. Leaf ranges in size to as small as 4.5 by 0.75 inches and as large as 9 by 4 inches.

*Margins.*—dentate.

*Color—top.*—Mat green (R.H.S.-146A).

*Color—bottom.*—Gray green, matt (R.H.S.-147B).

*Veins—top.*—spring-green, about the same as matrix.

*Veins—bottom.*—R.H.S.-145D.

*Petiole.*—Length 1.5 to 4.5 inches. Color—light green (R.H.S.-44B), blushes to orange (R.H.S.-164A) in full sun.

*Stipules.*—linear, deciduous.

Stem: Cane-like, pale green when young; blushing to light orange or red in full sun and in the Fall Basal cane diameter is approximately 2 inches for mature plants.

Height: Three to seven feet (depending upon length of growing season).

THE FLOWER

Blooming habit: Continuous and free blooming, late May–November (or until frost).

Corolla:

*Diameter.*—6 to 8 inches. The bloom is recurved and bell-shaped so the diameter is less than the sum of the length of two petals.

*Shape.*—Deeply flaredbell full petals overlapping basally and distally.

*Involucral bracts.*—Number — 11, sometimes 10.

*Color.*—medium green (R.H.S.-144A/146A).

Calyces:

*Number of sepals.*—Five, finely pubescent.

*Shape.*—Moderately dissected at about ⅝ inches from sepal apex, mosque-shaped with apical point at about 1.5 inches from base.

*Color.*—Pale green (R.H.S.-144A/146A).

Filaments:

*Color.*—White.

Stamens: Numerous.

Anthers:

*Color.*—Dark red brown (~R.H.S.-160A).

Stigma:

*Color.*—Pads pale yellow (~R.H.S.-160A). Pedicels and peduncle~(R.H.S.-155A).

*Number.*—Five, rounded, discoid, hairy.

Staminal column:

*Color.*—Creamy white without streaks (R.H.S.~155A).

*Length.*—2.5 inches. Antheriferous for the lower two-thirds of style. Base of pistil or very center of throat white(R.H.S.-155C), streaked with dark pink about one-fourth of the way up.

Pollen:

*Color.*—Pale yellow.

Petalage:

*Shape.*—Full, obovate, asymmetrical, apical point right or left of center, depending upon rotation of the individual flower.

*Size.*—About 4.5 to 5 inches (base of style to tip of petal) by 4 inches across, depending. Exact size depends upon preceding night temperature and culture.

*Aspect.*—Central one-third satiny, outer two-thirds translucent

*Texture.*—Moderately thick, about the weight of broadcloth.

*Color.*—Center eye zone: red (R.H.S.-53C), brightening to fuschia on the fringes of the eye (R.H.S.-58A). Inner petal: white (R.H.S.-155C). The whitest portion of the petal does not extend all the way across the individual petal and is overlapped by the pinkest part of its neighboring petal. If the petal rotation is overlapping to the left, the white portion of the inner petal will be on the right side of the petal, and vice versa. The white area does not have an abrubt border, but rather blends into the eye and petal colors and becomes less distinct as the overall flower color deepens towards the end of the day. Middle petal: blush (R.H.S.-69A/65C). Outer petal: pink (R.H.S.-65D/155C). Outer petal blushes darker as the day progresses. Back of petal: white (R.H.S.-155C). The overall effect is of a large, blushing classic hibiscus shape, nicely belled with a hint of ruffle. The degree of blushing is similar to that shown in *H. mutabilis* (Confederate Rose Hibiscus).

Flowers: Numerous, elegant; individual flowers last one day, two days in cooler weather.

Pedicle: Three to five inches; medium thickness; stiff. Peduncle articulated at or near 0.5–0.75 inches from the base of the pod.

GENERAL CHARACTERISTICS AND CULTURE

Blooming period: Late May to November (or frost) on the Texas Gulf Coast (Zone 9), July or early August to frost in cooler zones. From the onset of the blooming period the plant is seldom without flowers.

Hardiness: Root hardy to at least Zone 5 (further North if well mulched). Dormancy is apparently triggered by soil temperatures rather than by photoperiod. Research at Michigan State indicates that hibisci in this group are day-neutral bloomers.

Breaking action: Very tough. Immature stems bend and regrow.

Rooting: Excellent. Hormone optional, especially under mist.

Growth regulator: Not required. Optional for holding in pots for commercial nurseries.

Shipping tolerance: Excellent, especially as liners or at any size when dormant. Best shipped unstacked on individual shelves if not dormant.

I claim:

1. A new and distinct cultivar of Hibiscus plant, as shown and described.

* * * * *